United States Patent [19]

Noda

[11] Patent Number: 5,015,245

[45] Date of Patent: May 14, 1991

[54] DISPOSABLE SANITARY ARTICLES

[75] Inventor: Isao Noda, Fairfield, Ohio

[73] Assignee: The Procter & Gamble Company, Cincinnati, Ohio

[21] Appl. No.: 516,601

[22] Filed: Apr. 30, 1990

[51] Int. Cl.$^5$ .................. A61F 13/15; A61F 13/20; D21H 11/00; D21F 13/00

[52] U.S. Cl. .................... 604/367; 604/358; 604/368; 604/370; 162/164.3; 162/164.6; 162/169; 162/111

[58] Field of Search ............... 162/164.1, 164.3, 164.6, 162/169, 111, 166, 167; 604/367, 385, 370, 387, 368

[56] References Cited

U.S. PATENT DOCUMENTS

| | | | |
|---|---|---|---|
| 3,556,932 | 1/1971 | Coscia et al. | 162/166 |
| 3,556,933 | 1/1971 | Williams et al. | 162/167 |
| 3,700,623 | 10/1972 | Keim | 260/80.3 |
| 3,772,076 | 11/1973 | Keim | 117/155 |
| 3,860,003 | 1/1975 | Buell | 128/287 |
| 3,966,684 | 6/1976 | Espy et al. | 162/164.3 |
| 4,054,542 | 10/1977 | Buekman et al. | 162/164.3 |
| 4,129,528 | 12/1978 | Petrovich et al. | 162/164.3 |
| 4,233,411 | 11/1980 | Ballweber et al. | 162/164.3 |
| 4,510,019 | 4/1985 | Bartelloni | 162/169 |
| 4,584,357 | 4/1986 | Harding | 162/164.3 |
| 4,589,876 | 5/1986 | Van Tilberg | 604/385 R |
| 4,610,678 | 9/1986 | Weisman et al. | 604/368 |
| 4,687,478 | 8/1987 | Van Tilberg | 604/387 |
| 4,808,178 | 2/1989 | Aziz | 604/385.2 |
| 4,900,317 | 2/1990 | Buell | 604/370 |

*Primary Examiner*—Alan Cannon
*Assistant Examiner*—Elizabeth M. Burke
*Attorney, Agent, or Firm*—Jerry J. Yetter; Richard C Witte; Thomas H. O'Flaherty

[57] ABSTRACT

Disposable sanitary articles comprise paper treated with polycationic latexes as wet-strength agents. The paper has sufficient wet strength that it can serve as the backsheet for absorbent articles, garments, and the like. Thus, KYMENE is reacted, for example, with acrylic acid and cross-linked with styrene/butadiene to provide a polycationic latex which is used to treat paper to enhance its wet strength. Diapers, sanitary napkins, pantiliners, and the like, prepared from the foregoing materials are disclosed.

11 Claims, No Drawings

DISPOSABLE SANITARY ARTICLES

TECHNICAL FIELD

The present invention relates to disposable absorbent articles such as diapers, sanitary napkins, pantiliners, and the like, which are especially adapted for absorbing various body fluids. The articles herein are prepared using paper-based backsheet materials which are designed to enhance their disposability.

BACKGROUND OF THE INVENTION

A wide variety of absorbent structures designed to be efficient for the absorption of body fluids such as blood, urine, menses, and the like, are known. Disposable products of this type generally comprise some sort of fluid-permeable topsheet material, an absorbent core, and a fluid-impermeable backsheet material.

Heretofore, such absorbent structures have been prepared using, for example, topsheet materials prepared from woven, nonwoven, or porous formed-film polyethylene or polypropylene materials. Backsheet materials typically comprise flexible polyethylene sheets. Absorbent core materials typically comprise wood pulp fibers or wood pulp fibers in combination with absorbent gelling materials.

One aspect of such sanitary products which has recently been considered is their disposability. Although such products largely comprise materials which would be expected ultimately to degrade, and although products of this type contribute only a very small percentage of the total solid waste materials generated by consumers each year, nevertheless there is currently a perceived need to devise such disposable products from materials which degrade relatively quickly, thereby lessening their bulk.

Various attempts have been made to provide modified polymeric backsheets which would be more degradable than backsheet materials currently in use. Alternatively, it might seem reasonable to use paper backsheets. However, most paper sheets have too little wet strength to be useful in articles such as diapers, and the like, which must function in the presence of large amounts of moisture. While some relatively water-stable papers are known, they are generally too stiff in their dry state to provide the quality of disposable articles the consumer has come to expect.

More particularly, the present invention employs a paper backsheet which is treated with a polycationic latex material, as described hereinafter, which substantially enhances the wet strength of said paper, but without undesirably enhancing its dry strength to the extent that the resulting article is unattractively stiff or "crinkly". Stated succinctly, the practice of the present invention employs a new type of treated paper as the backsheet for such disposable articles.

BACKGROUND ART

U.S. Pat. Nos. 3,700,623 and 3,772,076, both to Keim, relate to wet-strength resins of the KYMENE type to treat paper. See also U.S. Pat. Nos. 3,556,932 and 3,556,933, relating to other wet-strength resins.

A large number of U.S. patents relate to the design and manufacture of disposable sanitary articles of various types, and reference can be made to these for designs, dimensions and manufacturing equipment for such articles. U.S. Pat. Nos. 4,610,678, 3,860,003, 4,900,317, 4,589,876, 4,808,178 and 4,687,478 are illustrative and are incorporated herein by reference.

SUMMARY OF THE INVENTION

The present invention encompasses absorbent structures comprising a topsheet, a backsheet, and an absorbent core interposed between said topsheet and backsheet, wherein said backsheet is a paper sheet, or the like, comprising multiple cellulosic fibers and a wet-strength agent which comprises a water-insoluble latex composition comprising the reaction product of a cationic polyamide/polyamine/epichlorohydrin wet-strength resin and a reactant (electrophiles or nucleophiles can be used) comprising an unsaturated polymerizable hydrocarbon moiety, said reaction product being co-polymerized with latex-forming polymerizable monomers or oligomers. Preferred latex-forming polymerizable monomers or oligomers used in said wet-strength agent are selected from the group consisting of styrene, 1,3-butadiene, isoprene, propylene, ethylene, and mixtures thereof.

Highly preferred absorbent structures herein are those wherein said paper backsheet comprises cellulosic fibers and a wet-strength agent comprising the reaction product of a wet strength resin containing repeat units of the general structural type

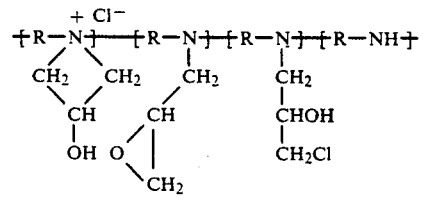

wherein R is

and a carboxylate (or carboxylate-derived) reactant, said reaction product being co-polymerized with latex-forming polymerizable monomers or oligomers. The carboxylate reactant used in said wet-strength agent is preferably a member selected from the group consisting of acrylates, methacrylates, itaconates, vinyl benzoates, unsaturated epoxides such as glycidyl methacrylate, unsaturated chlorohydrins such as chlorohydrin methacrylate, unsaturated fatty acids and their reactive derivatives, e.g., acid halides and anhydrides, and mixtures thereof. The latex-forming polymers or oligomers preferably used in said wet-strength agent are selected from the group consisting of styrene, 1,3-butadiene, isoprene, propylene, ethylene, and mixtures thereof. Vinyl acetate, methyl acrylate, methyl methacrylate, and t-butyl acrylate can also be used.

Preferred absorbent structures herein are those wherein said wet-strength agent comprises the reaction product of said cationic wet-strength resin and a reactant selected from acrylic acid, methacrylic acid, glycidyl methacrylate, and mixtures thereof, said reaction product being co-polymerized with styrene, 1,3-butadiene, or mixtures thereof.

A typical absorbent structure according to this invention is one wherein said wet-strength agent comprises from about 5% to about 30% by weight of said paper backsheet, and preferably comprises at least about 10% by weight of said paper backsheet.

Preferred absorbent structures herein are employed as disposable sanitary articles such as disposable diapers, sanitary napkins, adult incontinence garments, pantiliners, and the like. Preferred articles herein use an absorbent core which comprises an absorbent gelling material. For use in such articles, the absorbent gelling material is dispersed in the form of a powder in the otherwise fibrous absorbent core. In an alternate mode, the absorbent gelling material is used in the form of fibers in an absorbent core which otherwise comprises cellulosic fibers.

In yet another aspect, the invention encompasses disposable absorbent articles, as noted above, comprising a water-permeable topsheet, a paper backsheet, as noted above, and an absorbent core, said structures being characterized in that said absorbent core comprises oxidized cellulose. Typically, the oxidized cellulose comprises at least 16% carboxyl groups.

All percentages, ratios and proportions herein are by weight, unless otherwise specified.

DETAILED DESCRIPTION

The present invention relates to the manufacture of diapers, sanitary napkins, pantiliners, and the like, all of which have been described in great detail in patents and other literature. A wide variety of such articles are commercially available. It is to be understood that this invention does not relate to the manufacture of any particular type, shape or style of such articles; rather, the invention herein relates to the particular choice of backsheet materials which can be used in the manufacture of such articles to make them more disposable.

I. Wet-Strength Agent - The polyamide/polyamine/epichlorohydrin wet-strength resins used to prepare the wet-strength agents employed herein are fully described by Carr, Doane, Hamerstrand and Hofreiter, in an article appearing in the Journal of Applied Polymer Science Vol. 17, pp 721–735 (1973). Such resins are available as KYMENE (e.g., KYMENE 557) from Hercules, Inc. A commercial synthesis of such resins from adipic acid, diethylene thiamine and epichlorohydrin is described in the Carr et al publication, ibid., and is U.S. Pat. No. 2,926,154 (Feb. 23, 1960) to G. I. Keim. Reference can be made to these publications for further details regarding the preparation of polyamide/polyamine/epichlorohydrin resins of the type employed to prepare the polycationic latexes herein.

For use herein, the aforesaid resin is reacted in such a way as to introduce a polymerizable hydrocarbon moiety into the resin's structure. Such moiety can be co-polymerized with other polymerizable latex-forming monomers or oligomers to form a latex incorporating the resin. The resulting latex is polycationic, by virtue of the presence of the resin's polycationic substituents.

While not intending to be bound by theory, it is reasonable to speculate that the overall reaction involves the following, wherein M-X is a reactant comprising a reactive group X which can be, for example, carboxylate (preferred), amine, alkyl halide, chlorohydrin, epoxide, xanthate, acid anhydride, or the like, and wherein M contains at least one —C=C— bond, typically a $C_2$–$C_{16}$ unsaturated hydrocarbyl group, preferably $C_2$–$C_6$. Examples include: acrylate, methacrylate, vinyl benzoate or other vinyl groups, unsaturated fatty acids and other derivatives thereof, and the like. The reaction could occur at the 4-membered ring the epoxide or chloride of KYMENE, with, for example, acrylic acid, to produce a structure of the type shown below:

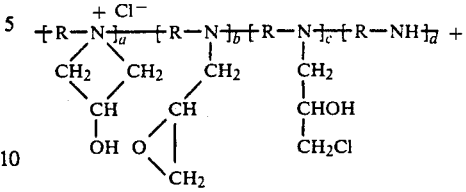

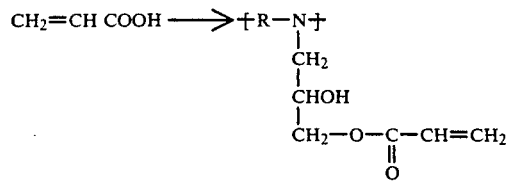

wherein a, b, c and d are each integers typically in the range of 20–500 and R is as disclosed hereinabove. Alternatively, the OH moieties and/or the residual secondary amine of KYMENE are available as reaction sites. As an example, acryloyl chloride could react with KYMENE to produce the structure below:

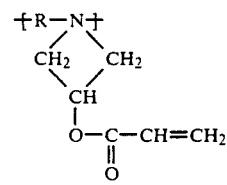

and glycidyl methacrylate could react with KYMENE to produce the structure below:

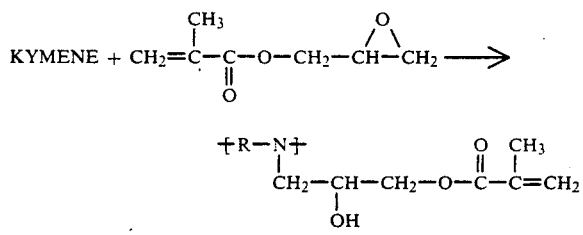

Whatever the mechanism of reaction, the unsaturated hydrocarbon moiety is thus attached to the KYMENE and is available to react with various latex-forming monomers or oligomers, thereby incorporating the KYMENE into and onto the resulting latex particles.

To illustrate the reaction further, KYMENE can be reacted with a member selected from the group consisting of vinyl benzoic acid, itaconic acid, oleic acid, linoleic acid, 3-bromopropyl acrylate, dimethylaminopropyl acrylate, acrylolyl chloride, itaconic anhydride, the methyl ester of acrylic acid, and mixtures thereof, and the reaction product co-polymerized with a member selected from the group consisting of styrene, 1,3-butadiene, isoprene, propylene, ethylene, methyl acrylate, vinyl acetate, methyl methacrylate, t-butyl methacrylate, and mixtures thereof, to provide polycationic latexes.

While the Examples disclosed hereinafter provide more specific details, the following general principles for carrying out such reactions are provided for assistance to the formulator. The reactions are conveniently carried out in water. The reaction temperatures can be in the range of about 30° C. to about 100° C., but a 60° C. reaction temperature is convenient. Reaction times can vary according to the temperature selected but reaction at 60° C. for 40 hours is convenient for laboratory syntheses. An emulsifier, e.g., oleyl ethoxylate as VOLPO-20 (Croda, Inc.), can be used in the reaction mixture, and some of this may be co-polymerized into the latex. In any event, the presence of the emulsifier results in a desirably fine suspension of the latex particles in the reaction medium. On a laboratory scale, it is convenient to use sufficient materials to provide a solids content of the final latex suspension in the range from about 10% to about 25% (wt.).

The latex compositions prepared according to such procedures are in the form of particles having an average size (sieve analysis) in the range of from about 10 nm to about 500 nm or to about several microns, preferably about 50 nm to about 500 nm. Such particles are conveniently formed as aqueous dispersions by the procedures disclosed hereinafter. The resulting dispersions can be used directly to treat paper to prepare the paper backsheets used in the practice of this invention. The following Examples illustrate the preparation of the polycationic latexes, but are not intended to be limiting thereof.

EXAMPLE I
KYMEME/Acrylic Acid/Styrene/Butadiene Latex

| Reagents | Amount (grams) |
|---|---|
| VOLPO-20 | 0.322 |
| V-50* | 0.072 |
| KYMENE** | 0.722 |
| Acrylic Acid | 0.14 |
| Styrene | 2.86 |
| 1,3-Butadiene | 4.29 |
| Distilled water as reaction medium | 50 mls |

*V-50 initiator is 2,2' azobis(2-amidopropane) dihydrochloride available from WAKO, USA.
**As 5.5 g. of 13% solution.

The water reaction medium is sparged for 30 minutes with argon prior to use. A 250 ml glass reaction bottle equipped with a magnetic stir bar is flushed with nitrogen for 5 minutes. The KYMENE, VOLPO-20, V-50 initiator and distilled water are placed in the reaction bottle, which is sealed with a rubber gasket and two-holed bottle cap. The mixture is argon sparged for 30 minutes.

The acrylic acid is added using a syringe and the styrene is added using a syringe. The reaction bottle is placed in an ice bath. The 1,3-butadiene is condensed in dry ice. Using a double-ended syringe and argon pressure, the 1,3-butadiene is added to the reaction vessel. A rubber septum is wired in place over the bottle cap and the reaction bottle is placed in an oil bath at 60° C. for 40 hours, with slow stirring. At the end of this time, the reaction product is pulled and strained through a fine wire sieve to provide a suspension of a captioned latex at a solids content of 13.5%.

EXAMPLE II

The reaction of Example I is repeated under the same conditions, but using 0.772 g of KYMENE and 0.358 g of acrylic acid. The reaction product is a 12.8% polycationic latex suspension.

EXAMPLE III

The reaction of Example I is repeated, but with the amount of KYMENE increased to 1.44 g (11.1 g of 13% solution). The reaction product is a 11.5% solids suspension of polycationic latex. In an alternative mode, the KYMENE level can be decreased to 2.77 g of a 13% (wt.) KYMENE solution to provide a polycationic latex suspension (13.6% wt. solids).

EXAMPLE IV

Following the procedure of Example I, a polycationic latex is prepared, but with the substitution of methacrylic acid (0.14 g) for the acrylic acid used in Example I, and with the use of 0.722 g of KYMENE. The reaction is allowed to proceed for 26 hours at 60° C. The reaction product is an aqueous suspension of a polycationic latex.

EXAMPLE V

Following the procedure of Example I, a polycationic latex is prepared, but with the substitution of 0.14 g of glycidyl methacrylate for the acrylic acid of Example I. The reaction product is an aqueous suspension of the polycationic latex.

EXAMPLE VI

Preparation of a Handsheet 2.65 g (2.50 g dry wt.) unrefined Northern Softwood Kraft (NSK) pulp is dispersed in 500 ml tap water at ambient pH (ca. 7.5).

5.0% (0.984 g) of the polycationic latex of Example I is added to the pulp slurry and stirred for 30 minutes.

The handsheet is made on a standard Deckle Box using tap water at ambient pH (ca. 7.5) and dried on a drum dryer at 110°-115° C.

EXAMPLE VII

The applicability of a polycationic latex as a wet-strength additive for a continuous papermaking process is as follows. Approximately 220 kg (dry weight) of refined northern softwood Kraft pulp is dispersed in water at the consistency of about 2.5% and kept in a stirred holding tank. About 400 liters of cationic latex prepared according to Example I are added to the pulp to achieve the wet-end deposition of the binder.

The latex-treated pulp is then fed to a pilot scale paper machine (equipped with normal papermaking process components, such as headbox, forming wire, and continuous dryer) at a rate of about 80 l/min. The paper machine is operated at the production speed of 200 m/min.

The latex content of the final paper products can be measured by x-ray fluorescence analysis. The analysis is done by brominating the unsaturated double bonds of a styrene-butadiene rubber component of the latex and then measuring the x-ray fluorescence intensity. The estimated latex add-on level for the sample measured by this method is on the order of 11-12%. The wet strength of the latex-containing paper product produced by a continuous pilot paper machine can be determined by measuring the tensile strength required to tear a one-inch-wide strip of paper product after the sample is soaked in water.

EXAMPLE VIII

A disposable baby diaper according to this invention is prepared as follows. The dimensions listed are for a diaper intended for use with a child in the 6-10 kilogram size range. These dimensions can be modified proportionately for different size children, or for adult incontinence briefs, according to standard practice.

1. Backsheet: paper sheet according to Example VII; width at top and bottom 33 cm; notched inwardly on both sides to a width-at-center of 28.5 cm; length 50.2 cm.
2. Topsheet: nonwoven fabric scrim comprising lactate/glycolate co-polyester fibers; width at top and bottom 33 cm; notched inwardly on both sides to a width-at-center of 28.5 cm; length 50.2 cm.
3. Absorbent core: oxidized cellulose (16-24% carboxyl); 8.4 mm thick, calendered; width at top and bottom 28.6 cm; notched inwardly at both sides to a width-at-center of 10.2 cm; length 44.5 cm; total 3.5 g polyacrylate absorbent gelling material particles dispensed throughout cellulose core material.
4. Elastic leg bands: four individual rubber strips (2 per side); width 4.77 mm; length 370 mm; thickness 0.178 mm (all the foregoing dimensions being in the relaxed state).

The diaper of Example VI is prepared in standard fashion by positioning the core material covered with the topsheet on the backsheet and gluing.

The elastic bands (designated "inner" and "outer", corresponding to the bands closest to, and farthest from, the core, respectively) are stretched to ca. 50.2 cm and positioned between the topsheet/backsheet along each longitudinal side (2 bands per side) of the core. The inner bands along each side are positioned ca. 55 mm from the narrowest width of the core (measured from the inner edge of the elastic band). This provides a spacing element along each side of the diaper comprising the flexible topsheet/backsheet material between the inner elastic and the curved edge of the core. The inner bands are glued down along their length in the stretched state. The outer bands are positioned ca. 13 mm from the inner bands, and are glued down along their length in the stretched state. The topsheet/backsheet assembly is flexible, and the glued-down bands contract to elasticize the sides of the diaper.

EXAMPLE IX

A lightweight pantiliner suitable for use between menstrual periods comprises a pad (surface area 117 $cm^2$; SSK air felt 3.0 g) containing 1.0 g of absorbent gelling material particles (commercial polyacrylate; Nippon Shokubai); said pad being interposed between a porous formed-film topsheet according to U.S. Pat. No. 4,463,045 and a backsheet which comprises a paper sheet prepared according to Example VI.

EXAMPLE X

A catamenial product in the form of a sanitary napkin having two flaps extending outward from its absorbent core is prepared using an absorbent pad (surface area 117 $cm^2$; 8.5 g SSK air felt) per the design of U.S. Pat. No. 4,687,478, Van Tillburg, Aug. 18, 1987. The backsheet comprises a paper sheet comprising ca. 20% by weight of the latex of Example III, and the topsheet comprises a nonwoven scrim of polylactate fibers.

EXAMPLE XI

The sanitary napkin of Example X is modified by replacing the topsheet with a porous nonglossy formed film, per U.S. Pat. No. 4,687,478, and using a backsheet comprising a paper sheet comprising 25% by weight of the latex of Example II.

II. Articles with Absorbent Cores Employing Wet-Strength Agent and Polyanionic Materials - The polycationic latex wet-strength agents herein can be used in paper articles, and the like, which contain various anionic materials, especially super-sorbents, without undesirably interfering with the properties of said anionic materials. This allows the preparation of not only standard fibrous batts containing "super-sorbers" for use as absorbent cores, but also for the preparation of super-thin absorbent cores having good wet-strength properties and which, in essence, comprise a sheet or sheets of super-sorbent paper which are about as thick as a conventional disposable paper towel (10-30 mils).

Super-absorbent materials (also referred to as "absorbent gelling materials" or "super-sorbers") which can be used in combination with the polycationic latexes herein comprise, by way of example but not limitation, the class of acrylate and starch-acrylate materials which have become widely known for use in disposable diapers. Such materials are commercially available in powdered form under several trade names, such as SANWET, AQUALIC, FAVOR and ABSORB. Further details regarding such materials are available from trade literature and U.S. Pat. No. 4,610,678.

Polyanionic super-absorbents can also be prepared in fibrous form, and super-absorbent fibers are especially useful when preparing paper sheets with high water absorption capacities. Super-absorbent fibers are not as readily available in commerce as the powder-form materials noted above; accordingly, the following disclosure describes representative syntheses of such fibers.

One example of a polyanionic, chemically modified fiber having high absorbent properties comprises, chemically bonded together, (a) a cellulosic fiber, very preferably a Kraft or chemithermomechanical fiber; (b) a poly(acrylate-co-itaconate) copolymer, preferably having a relatively high acrylate content and a relatively low itaconate content; and (c) a polyol, very preferably a polyethylene glycol.

Another example of a polyanionic, chemically modified fiber having a water absorbency and retention value in the range from about 15 g/g to about 100 g/g comprises, chemically bonded together:

(a) a cellulosic fiber selected from the group consisting of chemithermomechanical pulp fiber, bleached hardwood Kraft pulp fiber, bleached softwood Kraft pulp fiber, unbleached hardwood Kraft pulp fiber, unbleached softwood Kraft pulp fiber, bleached softwood sulfite pulp fiber, bleached hardwood sulfite pulp fiber, unbleached softwood sulfite pulp fiber, unbleached hardwood sulfite pulp fiber, cotton linters, mercerized dissolving pulp fiber, unmercerized dissolving pulp fiber, and mixtures thereof;
(b) a poly(methyl vinyl ether-co-maleate) 1:1 copolymer having a number average molecular weight in the range from about 39,000 to about 80,000, and
(c) a polyol; wherein the proportion by weight of said poly(methyl vinyl ether-co-maleate) copolymer to said polyol is from about 250:1 to about 3:1 and the weight of said poly(methyl vinyl ether-comaleate)

copolymer plus said polyol per unit weight of said cellulosic fiber, (a), is in the range from about 0.3 to about 2, the poly(methyl vinyl ether-co-maleate) copolymer weight being expressed on an acid equivalent basis.

The following Examples illustrate the formation of polyanionic fibers useful in the practice of this invention.

EXAMPLE XII

Starting-Materials

Acrylic acid (Polysciences Inc., Warrington, Pa.) is vacuum distilled through a Vigreux column and is preferably used fresh in subsequent operations, e.g., within one day of distillation. Itaconic acid (Aldrich Chemical Co., Milwaukee, Wis.) is obtained in 99%+purity and is used as received. The free-radical initiator 2,2'-azobis(2-amidinopropane) dihydrochloride (WAKO V-50, Wako Pure Chemical Industries, Osaka, Japan) is also used as received. Unless otherwise noted, water is triply distilled. Where polymers are dialyzed, the dialysis membrane is obtained from Spectrum Medical Industries, Inc., Los Angeles, Calif.

Polyethylene glycols (these preferred polyols are commonly known as "PEG", various suppliers being suitable) as used in the Examples have nominal molecular weights of 200, 1000, 1500, 3350, and 6800. PEG 200 is obtained from Polysciences Inc., Warrington, Pa. PEG 1000, PEG 1500 and PEG 6800 are obtained from Scientific Polymer Products, Inc., Ontario, N.Y. PEG 3350 is obtained from Sigma Chemical Co., St. Louis, Mo.

Southern softwood Kraft pulp and northern softwood Kraft pulp are obtained from P&G Cellulose, Memphis, Tenn. Chemithermomechanical pulp is obtained from Quesnel Paper Co., Quesnel, B.C., Canada.

Preparation of a poly(acrylate-co-itaconate) copolymer suitable for use in making a super-absorbent fiber (90 mole % acrylate, 10 mole % itaconate)

Acrylic acid (20.000 g, 0.27755 mole), itaconic acid (4.0121 g, 0.038386 mole), Wako V-50 (0.0837 g, 0.308 millimole), and 150 ml of water which has been acidified to pH 2.0 with hydrochloric acid are added to a 250 ml three-necked round-bottomed flask. The necks are fitted with a thermometer, a stopper, and a gas inlet/outlet adapter capable of bubbling gas through a liquid in the flask and venting it. The solution is deaerated by passage of nitrogen gas and is then placed under an atmosphere of argon. The solution is heated to 55° C. and is maintained at this temperature for 15 hours. The viscous solution of copolymer is cooled to ambient temperature and is dialyzed overnight against water (Spectrapor 3 tubing with molecular weight cut-off at 3500) to remove any unreacted monomers. The dialyzed solution is freeze dried to afford 23.00 g of poly(acrylate-co-itaconate) copolymer, acid form, as a colorless solid.

Preparation of Fiber

The poly(acrylate-co-itaconate) copolymer (2.00 g) is dissolved by adding it portionwise to 20 ml of water while stirring and heating to 65°-70° C. To the solution is added polyethylene glycol (0.334 g, nominal molecular weight 3350) predissolved in 5 ml of water. Stirring is continued until dissolution is complete. The resulting aqueous medium is cooled to ambient temperature and the pH is adjusted to 3.00 (the "pH of the aqueous medium" referred to elsewhere herein) with Molar sodium hydroxide. Loose fibers of southern softwood Kraft pulp (2.00 g bone-dry weight basis) are added. The resulting slurry is thoroughly mixed and is spread out into a thin layer on a 6-inch diameter watch glass of thickness about 3 mm. The slurry layer is dried in an oven at 65°-70° C., a temperature selected to minimize or avoid crosslinking reactions, and is then cured by placing the watch glass in an oven preheated to a curing temperature of 130° C. The curing time is 11.5 minutes. The layer, now about 1 mm thick, is cooled to ambient temperature. This yields fiber in the acid form, which is not particularly absorbent. The fiber is then repulped. In practice it is convenient to soak it with distilled water, tear it into small pieces and add it to 400 ml of distilled water. After further stirring (e.g., overnight) the pH of the mixture is adjusted to 2.0 with hydrochloric acid and it is mixed in a Waring Blender in two steps wherein (1) the blender is run on low speed for 5.0 minutes at 50% power and (2) the blender is run for 1.0 minute on low speed at full power. The fibers, still in the acid form, are collected by suction filtration in a Buchner funnel fitted with a handsheet forming wire, washed with 400 ml of water, and are re-suspended into 500 ml of water. The slurry pH is adjusted to 8.5 using 1 Molar sodium hydroxide in water. (Using potassium hydroxide or lithium hydroxide instead of sodium hydroxide at this stage would result in the potassium or lithium form of the fibers.) Over two days, the pH is periodically checked and readjusted to 8.5 with sodium hydroxide. During this period, the fibers exchange to the sodium salt form, which is highly absorbent. Thus, the fibers swell. The fully swollen fibers are collected by suction filtration and are washed with distilled water.

EXAMPLE XIII

Starting-Materials

Poly(methyl vinyl ether-co-maleate) copolymers are obtained from GAF Chemicals Corp., Wayne, N.J. Suitable anhydride forms of the copolymers are GANTREZ AN-149, GANTREZ AN-169, and GANTREZ AN-179, having number average molecular weights, $M_n$, of 50,000, 67,000 and 80,000, respectively, as identified by GAF. The corresponding acid forms can be obtained by aqueous hydrolysis. A suitable acid-form copolymer directly obtainable commercially from the same supplier is GANTREZ S-97. It can be purchased either as a solid or as an aqueous solution.

Polyethylene glycols (these preferred polyols are commonly known as "PEG", various suppliers being suitable) as used in the Examples have nominal molecular weights of 200, 1000, 1500, 3350, and 6800. PEG 200 is obtained from Polysciences Inc., Warrington, Pa. PEG 1000, PEG 1500 and PEG 6800 are obtained from Scientific Polymer Products, Inc., Ontario, N.Y. PEG 3350 is obtained from Sigma Chemical Co., St. Louis, Mo.

Southern softwood Kraft (SSK) pulp and northern softwood Kraft (NSK), bleached hardwood aspen pulp, bleached hardwood sulfite pulp, cotton linters, bleached hardwood eucalyptus pulp, dissolving SSK (V-60), and mercerized dissolving SSK (V-5), are obtained from P&G Cellulose, Memphis, Tenn. Chemithermomechanical pulp is obtained from Quesnel Paper Co., Quesnel, British Columbia, Canada.

Unless otherwise noted, acetone is reagent grade and water is triply distilled.

Preparation of Fiber

The GANTREZ S-97 (3.35 g) is dissolved by adding it portion-wise to 30 ml of water which has been acidified to pH 2.00 with 1 Molar hydrochloric acid while stirring and heating to 65°–70° C. To the solution is added polyethylene glycol (0.500 g, nominal molecular weight 3350). Stirring is continued until dissolution is complete. The resulting aqueous medium is now cooled to ambient temperature. The pH of this medium (the "pH of the aqueous medium" referred to elsewhere herein) is measured to be 1.60. Loose fibers of chemi-thermomechanical pulp (3.00 g) are added. The resulting slurry is thoroughly mixed and is spread out into a thin layer on a piece of aluminum foil. The slurry layer is dried in an oven at 65°–70° C., a temperature selected to minimize or avoid crosslinking reactions. The layer, now about 1 mm thick, is removed from the foil and is cured by placing it in an oven preheated to a curing temperature of 130° C. The curing time is 6.5 minutes. The layer is cooled to ambient temperature. This yields raw fiber in the acid form, which is not particularly absorbent. The fiber is then repulped. In practice it is convenient to break it into small pieces and add it to 500 ml of distilled water. After further stirring (e.g., 1 hour) the pH of the mixture is adjusted to 2.0 with hydrochloric acid and it is mixed in a Waring Blender for 1 minute on low speed. The fibers, still in the acid form, are collected by suction filtration in a Buchner funnel fitted with a handsheet forming wire, are washed with 500 ml of water, and are re-suspended into 500 ml of water. The slurry pH is adjusted to 8.5 using 1 Molar sodium hydroxide in water. (Using potassium hydroxide or lithium hydroxide instead of sodium hydroxide at this stage would result in the potassium or lithium form of the fibers.) Over one day, the pH is periodically checked and readjusted to 8.5 with sodium hydroxide. During this period, the fibers exchange to the sodium salt form, which is highly absorbent. Thus, the fibers swell. The fully swollen fibers are collected by suction filtration and are washed with distilled water.

EXAMPLE XIV

Incorporation of the superabsorbent fibers into a paper sheet having good wet-strength properties is carried out as follows.

Preparation of Superabsorbent Layered Handsheet Paper

Two separate slurries are prepared comprising 1.06 g (1.0 g dry wt.) 40% wt. unrefined NSK pulp in 250 ml distilled water, adjusted to pH 8.5 (0.1 N sodium hydroxide).

The polycationic latex of Example I (0.652 g) is added to each of the two NSK/water slurries and stirred for 30 minutes.

The superabsorbent fiber of Example XII (0.5 g dry wt.) is slurried in 150 ml distilled water at pH 8.5 (1.0 N sodium hydroxide).

Each separate slurry is formed on the Deckle Box in distilled water at pH 8.5 and placed on a transfer fabric in the following order: top layer, 40%, sheet; middle layer, superabsorbent sheet; bottom layer, 40%, sheet.

Each layered sheet is transferred via a vacuum slit to a transfer sheet to form the finished paper handsheet. The finished handsheet is passed over a high vacuum twice and a second transfer sheet is placed on top of the finished sheet. The resulting sheets are passed over the drum dryer (155° C.) 10–12 times, until dry.

EXAMPLE XV

Mixed Furnish Handsheet Paper Containing Superabsorbent Fibers 2.0 g dry wt. unrefined NSK pulp is dispersed in 35.0 ml distilled water at pH 8.5 (0.1 N sodium hydroxide). 3.0% (1.304 g) of the polycationic latex of Example I is added to the NSK pulp dispersion and stirred for 30 minutes.

Separately, a dispersion is prepared comprising 20% super-absorbent fibers according to Example XIII and 150 ml distilled water at pH 8.5 (1.0 N sodium hydroxide).

The two slurries prepared in the foregoing manner are then combined and stirred for 15 minutes.

Following the procedure in Example VI, the handsheet is formed on the Deckle Box with distilled water at pH 8.5 (1.0 N sodium hydroxide). The handsheet is dried between two transfer fabrics on the drum dryer (115° C.) using 10–12 passes to achieve dryness.

EXAMPLE XVI

A pantiliner, or the like, comprises a paper backsheet comprising 22% wt. of the polycationic latex of Example V, an absorbent core comprising an absorbent sheet according to Example XV and a fluid-permeable topsheet comprising a scrim of non-woven polypropylene fibers.

EXAMPLE XVII

An ultra-thin sanitary napkin is prepared according to the article of Example XVI, but using tripled sheets according to Example XIV to comprise the absorbent core and using a formed-film topsheet according to U.S. Pat. No. 4,463,045 to replace the scrim topsheet.

EXAMPLE XVIII

An ultra-thin disposable diaper comprises a paper backsheet which is substantially urine-impervious by virtue of having been treated on its inner surface with 15%–25% by weight of said sheet of the polycationic latex of Example IV. The absorbent core comprises a 5-fold thickness of the superabsorbent paper of Example XV, and the topsheet comprises a urine-permeable sheet of nonwoven polypropylene fibers.

EXAMPLE XIX

While the Examples above illustrate the formation of polycationic latexes useful herein, it will be appreciated that the styrene/1,3-butadiene monomers used in Example I can be replaced by, for example: styrene isoprene (1:1 wt.); isoprene; and ethylene, respectively. Such examples are given here by way of illustration and not limitation.

What is claimed is:

1. An absorbent structure comprising a topsheet, a backsheet, and an absorbent core interposed between said topsheet and backsheet, wherein said backsheet is a paper sheet, or the like, comprising multiple cellulosic fibers and a wet-strength agent which comprises a water-insoluble latex composition comprising the reaction product of a cationic polyamide/polyamine/epichlorohydrin wet-strength resin and a reactant comprising an unsaturated polymerizable hydrocarbon moiety, said reaction product being co-polymerized with latex-forming polymerizable monomers or oligomers.

2. An absorbent structure according to claim 1 wherein the latex-forming polymerizable monomers or oligomers in said wet-strength agent are selected from the group consisting of styrene, 1,3-butadiene, and mixtures thereof.

3. An absorbent structure according to claim 1 wherein said paper backsheet comprises cellulosic fibers and a wet-strength agent comprising the reaction product of a wet strength resin containing repeat units of the general structural type

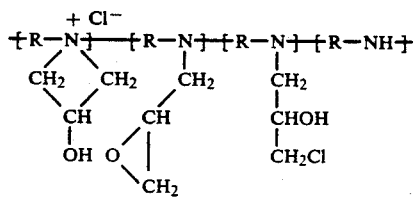

wherein R is

and X is an anion, and a carboxylate reactant, said reaction product being co-polymerized with latex-forming polymerizable monomers or oligomers.

4. An absorbent structure according to claim 3 wherein said carboxylate reactant in said wet-strength agent is a member selected from the group consisting of acrylic acid, methacrylic acid, glycidyl methacrylate, and mixtures thereof.

5. An absorbent structure according to claim 4 wherein said latex-forming polymers or oligomers in said wet-strength agent are selected from the group consisting of styrene, 1,3-butadiene, and mixtures thereof.

6. An absorbent structure according to claim 5, wherein said wet-strength agent comprises the reaction product of said cationic wet-strength resin and a carboxylate reactant selected from acrylic acid, methacrylic acid, glycidyl methacrylate, and mixtures thereof, said reaction product being co-polymerized with styrene, 1,3-butadiene, and mixtures thereof, said wet-strength agent comprising from about 5% to about 30% by weight of said paper backsheet.

7. An absorbent structure according to claim 6 wherein set wet-strength agent comprises at least about 10% by weight of said paper backsheet.

8. A disposable diaper, sanitary napkin, adult incontinence garment or pantiliner according to claim 1 wherein said absorbent core comprises an absorbent gelling material.

9. An article according to claim 8 wherein the absorbent gelling material is dispersed in the form of a powder in the otherwise fibrous absorbent core.

10. An article according to claim 8 wherein the absorbent gelling material is in the form of fibers in an absorbent core which otherwise comprises cellulosic fibers.

11. A disposable diaper, sanitary napkin, adult incontinence garment or pantiliner according to claim 1 wherein said absorbent core comprises oxidized cellulose.

* * * * *